(12) United States Patent
Sonobe et al.

(10) Patent No.: US 9,969,688 B2
(45) Date of Patent: May 15, 2018

(54) ROFLUMILAST PRODRUGS

(71) Applicant: HISAMITSU PHARMACEUTICAL CO., INC., Tosu-shi, Saga (JP)

(72) Inventors: Atsushi Sonobe, Tsukuba (JP); Takashi Yasukochi, Tsukuba (JP); Yasunori Takada, Tsukuba (JP); Kenji Atarashi, Tsukuba (JP); Motohiro Suzuki, Tsukuba (JP); Shinichi Yokota, Tsukuba (JP)

(73) Assignee: HISAMITSU PHARMACEUTICAL CO., INC., Tosu-shi, Saga (JP)

( * ) Notice: Subject to any disclaimer, the term of this patent is extended or adjusted under 35 U.S.C. 154(b) by 7 days.

(21) Appl. No.: 15/502,793

(22) PCT Filed: Oct. 21, 2015

(86) PCT No.: PCT/JP2015/079689
§ 371 (c)(1),
(2) Date: Feb. 9, 2017

(87) PCT Pub. No.: WO2016/063906
PCT Pub. Date: Apr. 28, 2016

(65) Prior Publication Data
US 2017/0233343 A1    Aug. 17, 2017

(30) Foreign Application Priority Data
Oct. 24, 2014  (JP) .................................. 2014-217205

(51) Int. Cl.
*C07D 213/75*    (2006.01)

(52) U.S. Cl.
CPC .................. *C07D 213/75* (2013.01)

(58) Field of Classification Search
CPC .................................................. C07D 213/75
See application file for complete search history.

(56) References Cited

U.S. PATENT DOCUMENTS

| | | |
|---|---|---|
| 5,712,298 A | 1/1998 | Amschler |
| 2006/0084684 A1 | 4/2006 | Bolle et al. |
| 2007/0259009 A1 | 11/2007 | Linder |
| 2013/0131123 A1 | 5/2013 | Dietrich et al. |

FOREIGN PATENT DOCUMENTS

| | | |
|---|---|---|
| JP | 11-139968 A | 5/1999 |
| JP | 2005-529930 A | 10/2005 |
| JP | 2008-513416 A | 5/2008 |
| JP | 2011-219364 A | 11/2011 |
| WO | 2011/163594 A2 | 12/2011 |
| WO | 2015/013715 A2 | 1/2015 |

OTHER PUBLICATIONS

Patrick S. Fier, et al., "Synthesis and Late-Stage Functionalization of Complex Molecules through C-H Fluorination and Nucleophilic Aromatic Substitution", Journal of the American Chemical Society, 2014, pp. 10139-10147, vol. 136, No. 28.
Eiji Mukai, et al., "Enhanced delivery of mitomycin C prodrugs through the skin", International Journal of Pharmaceuticals, 1985, pp. 95-103, vol. 25.
K.B. Sloan, et al., "Acyloxyamines as Prodrugs of Anti-inflammatory Carboxylic Acids for Improved Delivery Through Skin", Journal of Pharmaceutical Sciences, 1984, pp. 1734-1737, vol. 73, No. 12.
International Search Report of PCT/JP2015/079689, dated Jan. 19, 2016. [PCT/ISA/210].
International Preliminary Report on Patentability issued from the International Bureau in counterpart International Application No. PCT/JP2015/079689, dated May 4, 2017.
Communication dated Mar. 14, 2018 from the European Patent Office in counterpart application No. 15852038.7.

*Primary Examiner* — Noble E Jarrell
*Assistant Examiner* — John S Kenyon
(74) *Attorney, Agent, or Firm* — Sughrue Mion, PLLC

(57) ABSTRACT

The present invention provides a compound represented by the formula (I) or a pharmaceutically acceptable salt thereof:

[Chemical Formula 1]

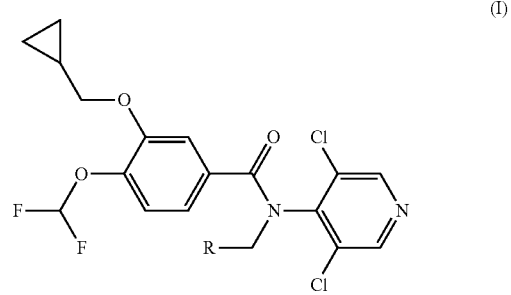

(I)

wherein R is a hydrogen atom, a $C_{1-6}$ alkyl group optionally substituted with one or more hydroxyl groups, a $C_{1-6}$ alkoxy group, or a cyano group.

10 Claims, 1 Drawing Sheet

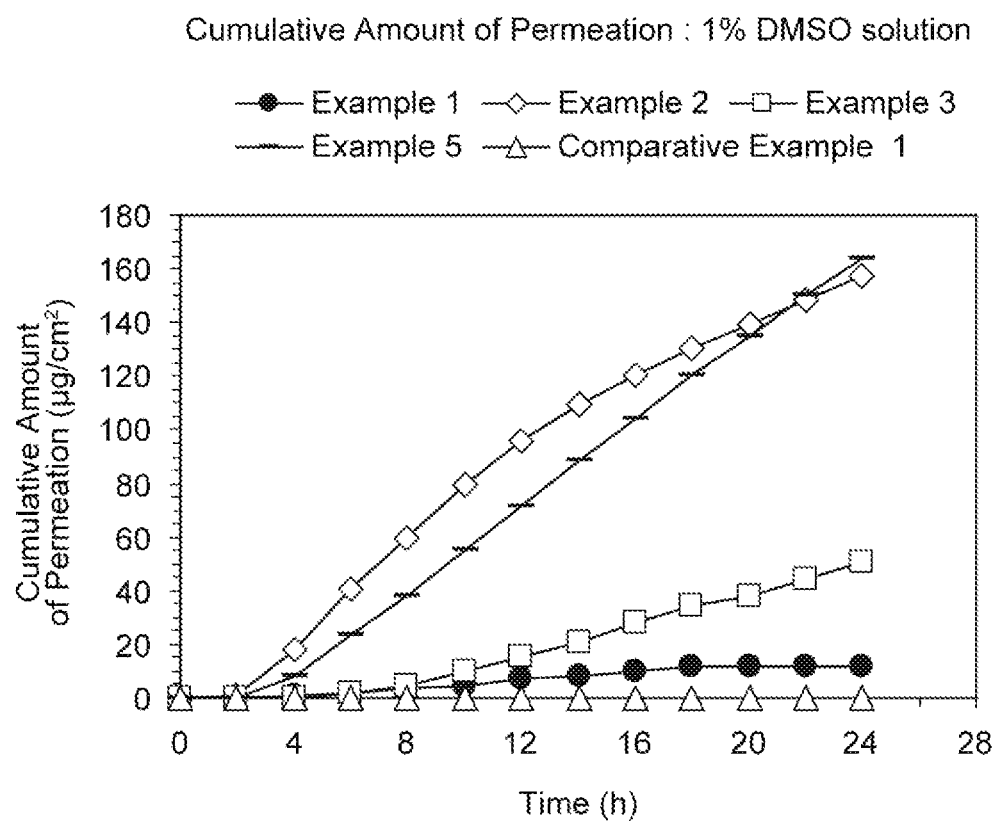

ROFLUMILAST PRODRUGS

CROSS REFERENCE TO RELATED APPLICATIONS

This application is a National Stage of International Application No. PCT/JP2015/079689 filed Oct. 21, 2015, claiming priority based on Japanese Patent Application No. 2014-217205, filed Oct. 24, 2014, the contents of all of which are incorporated herein by reference in their entirety.

TECHNICAL FIELD

The present invention relates to a prodrug.

BACKGROUND ART

Phosphodiesterase (PDE) inhibitors are known to be effective in treating inflammatory diseases. In particular, PDE4 inhibitors are effective in treating inflammatory diseases of respiratory tract including asthma or airway obstruction (e.g., chronic obstructive pulmonary disease (COPD)) (Patent Literature 1). Among them, N-(3,5-dichloropyrid-4-yl)-3-cyclopropylmethoxy-4-difluoromethoxy-benzamide (also referred to as roflumilast), which is a PDE4 inhibitor, is commercially available as an oral agent (trade name: Daxas (R)) in Europe and the United States (Patent Literature 2) and is recently investigated for possible application to aqueous medicinal preparations and transdermally absorbable preparations (Patent Literatures 3 to 5).

CITATION LIST

Patent Literature

Patent Literature 1: U.S. Pat. No. 5,712,298
Patent Literature 2: US 2013/0131123
Patent Literature 3: JP 2008-513416 A
Patent Literature 4: JP 2005-529930 A
Patent Literature 5: JP 011-219364 A

SUMMARY OF INVENTION

Technical Problem

Roflumilast is a very poorly water-soluble compound, which therefore requires particular works to allow roflumilast to be contained in a formulation in high concentration. Roflumilast also has poor skin permeability and thus is very difficult to be formulated into transdermally absorbable preparations.

Accordingly, an object of the present invention is to provide a compound or a salt thereof that has good water solubility and skin permeability and is metabolized rapidly to produce roflumilast in the body.

Solution to Problem

The present inventors, as a result of dedicated investigation, have found that introduction of a substituent into the nitrogen atom composing the benzamide moiety of roflumilast markedly alters the physical properties of the compound and improves water solubility and skin permeability, and finally have completed the present invention.

More specifically, the present invention provides (1) to (15) as follows:

(1) A compound represented by the formula (I) or a pharmaceutically acceptable salt thereof:

[Chemical Formula 1]

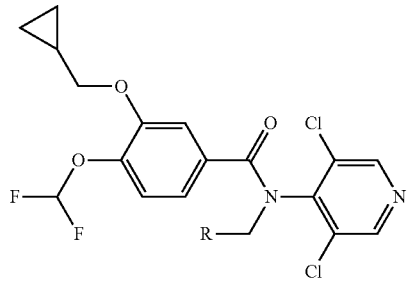

wherein R is a hydrogen atom, a $C_{1-6}$ alkyl group optionally substituted one or more hydroxyl groups, a $C_{1-6}$ alkoxy group, or a cyano group.

(2) The compound or pharmaceutically acceptable salt thereof according to (1), wherein R is a hydrogen atom, a $C_{1-6}$ alkyl group optionally substituted with one or more hydroxyl groups, or a cyano group.

(3) The compound or pharmaceutically acceptable salt thereof according to (1), wherein R is a hydrogen atom, a hydroxymethyl group, a methoxy group, or a cyano group.

(4) The compound or pharmaceutically acceptable salt thereof according to (1), wherein. R is a hydrogen atom, a hydroxymethyl group, or a cyano group.

(5) A pharmaceutical composition comprising the compound or pharmaceutically acceptable salt thereof according to any one of (1) to (4).

(6) The pharmaceutical composition according to (5), wherein the pharmaceutical composition is a PDE4 inhibitor.

(7) The pharmaceutical composition according to (5), wherein the pharmaceutical composition is a therapeutic agent for a disease or condition against which inhibiting PDE4 is effective.

(8) The pharmaceutical composition according to (7), wherein the disease or condition is a chronic obstructive pulmonary disease.

(9) A method for treating a disease or condition against which inhibiting PDE4 is effective, comprising administering the compound or pharmaceutically acceptable salt thereof according to any one of (1) to (4) to a subject in need thereof.

(10) The method for treating according to (9), wherein the disease or condition is a chronic obstructive pulmonary disease.

(11) Use of the compound or pharmaceutically acceptable salt thereof according to any one of (1) to (4) for manufacturing a pharmaceutical composition for treating a disease or condition against which inhibiting PDE4 is effective.

(12) The use according to (11), wherein the disease or condition is a chronic obstructive pulmonary disease.

(13) The compound or pharmaceutically acceptable salt thereof according to any one of (1) to (4) for use as an active ingredient of a pharmaceutical composition.

(14) The compound or pharmaceutically acceptable salt thereof according to (13), wherein the pharmaceutical composition is a PDE4 inhibitor,

(15) The compound or pharmaceutically acceptable salt thereof according to (13), wherein the pharmaceutical composition is a pharmaceutical composition for treating a disease or condition against which inhibiting PDE4 is effective.
(16) The compound or pharmaceutically acceptable salt thereof according to (15), wherein the disease or condition is a chronic obstructive pulmonary disease.

Advantageous Effects of Invention

A compound represented by the formula (I) or a pharmaceutically acceptable salt thereof according to the present invention has good water solubility and skin permeability and is capable of being metabolized rapidly to produce roflumilast in the body. Thus, the compound or pharmaceutically acceptable salt thereof according to the present invention has the advantage of ability to be used as an active ingredient in a wide variety of formulations including aqueous formulations and also the advantage of easy control of the concentration of roflumilast in blood due to rapid production of roflumilast after absorption into the body. In other words, the compound represented by the formula (I) or pharmaceutically acceptable salt thereof according to the present invention is useful as a prodrug of roflumilast.

Furthermore, the compound represented by the formula (I) or pharmaceutically acceptable salt thereof according to the present invention can be manufactured in a short step and in high yield from roflumilast.

BRIEF DESCRIPTION OF DRAWINGS

FIG. 1 is a graph showing skin permeability in Examples 1 to 3 and 5 and Comparative Example 1.

DESCRIPTION OF EMBODIMENTS

An embodiment of the present invention will be described below.

The present embodiment is a compound represented by the formula (I) (also referred to as compound (I) hereinafter) or a pharmaceutically acceptable salt thereof,

[Chemical Formula 2]

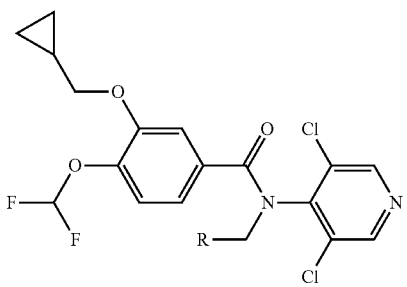

(I)

wherein R is a hydrogen atom, a $C_{1-6}$ alkyl group optionally substituted with one or more hydroxyl groups, a $C_{1-6}$ alkoxy group, or a cyano group.

The $C_{1-6}$ alkyl group refers to an alkyl group having one to six carbon atoms. Examples of $C_{1-6}$ alkyl groups include a methyl group, an ethyl group, an n-propyl group, an isopropyl group, an n-butyl group, an isobutyl group, a tert-butyl group, an n-pentyl group, a 2-pentyl group, a 3-pentyl group, an n-hexyl group, a 2-hexyl group, and a 3-hexyl group.

The $C_{1-6}$ alkyl group may be optionally substituted with one or more hydroxyl groups. Examples of $C_{1-6}$ alkyl groups substituted with one or more hydroxyl groups include a hydroxymethyl group, a 1-hydroxy ethyl group, a 2-hydroxyethyl group, and a 2,3-dihydroxypropan-1-yl group.

The $C_{1-6}$ alkoxy group refers to an alkoxy group having one to six carbon atoms. Examples of $C_{1-6}$ alkoxy groups include a methoxy group, an ethoxy group, an n-propyloxy group, an isopropyloxy group, an n-butyloxy group, an isobutyloxy group, a tert-butyloxy group, an n-pentyloxy group, a 2-pentyloxy group, a 3-pentyloxy group, an n-hexyloxy group, a 2-hexyloxy group, and a 3-hexyloxy group.

The pharmaceutically acceptable salt is any salt of inorganic acids or organic acids and is not particularly limited as long as it is a salt that can be used in the field of pharmaceuticals. Examples of inorganic acids include hydrochloric acid, hydrobromic acid, phosphoric acid, sulfuric acid, and nitric acid. Examples of organic acids include carboxylic acids such as acetic acid, citric acid, fumaric acid, maleic acid, tartaric acid, benzoic acid, and pamoic acid; sulfonic acids such as methane sulfonic acid, benzene sulfonic acid, and toluene sulfonic acid; acidic amino acids such as glutamic acid and aspartic acid; carbonic acid; and bicarbonic acid.

In the compound (I), R is a hydrogen atom, a $C_{1-6}$ alkyl group optionally substituted with one or more hydroxyl groups, a $C_{1-6}$ alkoxy group, or a cyano group, preferably a hydrogen atom, a $C_{1-3}$ alkyl group substituted with one or more hydroxyl groups, a $C_{1-3}$ alkoxy group, or a cyano group, more preferably a hydrogen atom, a hydroxymethyl group, a 2,3-dihydroxypropan-1-yl group, a 3-hydroxypropan-1-yl group, a methoxy group, or a cyano group, and particularly preferably a hydrogen atom, a hydroxymethyl group, a methoxy group, or a cyano group.

Examples of particularly preferred compounds (I) include
N-cyanomethyl-N-(3,5-dichloropyrid-4-yl)-3-cyclopropyl-methoxy-4-difluoromethoxybenzamide
N-(3,5-dichloropyrid-4-yl)-N-(2-hydroxyethyl)-3-cyclopropylmethoxy-4-difluoromethoxybenzamide,
N-(3,5-dichloropyrid-4-yl)-N-methyl-3-cyclopropyl-methoxy-4-difluoromethoxybenzamide,
N-(3,5-dichloropyrid-4-yl)-N-(2,3-dihydroxypropan-1-yl)-3-cyclopropylmethoxy-4-difluoromethoxybenzamide,
N-(3,5-dichloropyrid-4-yl)-N-(3-hydroxypropan-1-yl)-3-cyclopropylmethoxy-4-difluoromethoxybenzamide, and
N-(3,5-dichloropyrid-4-yl)-N-methoxymethyl-3-cyclopropylmethoxy-4-difluoromethoxybenzamide.

Next, a method of manufacturing a compound (I) of the present invention will be described.

A compound (I) can be manufactured by reacting roflumilast with a compound (II) in the presence of a base.

[Chemical Formula 3]

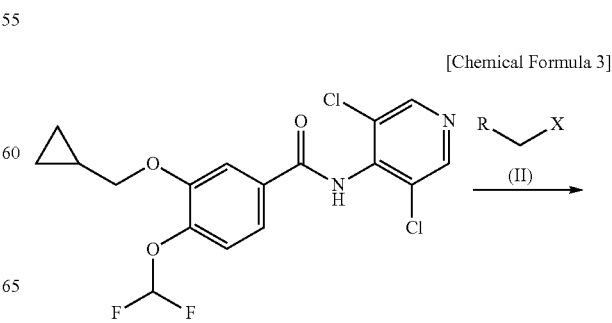

(II)

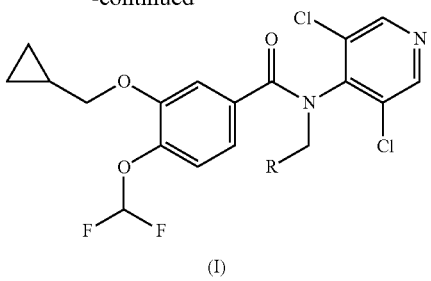

The base used in the reaction described above is not particularly limited as long as the base can perform deprotonation of benzamide moiety on the nitrogen atom thereof. Examples of bases include metal hydroxides such as sodium hydroxide and potassium hydroxide; metal alkoxides such as sodium methoxide and potassium tert-butoxide; metal hydrides such as sodium hydride and potassium hydride; metal amides such as sodium hexamethyldisilazide and lithium hexamethyldisilazide; and metal alkyl compounds such as butyl lithium and isopropyl magnesium bromide. A preferred base is sodium hydride.

In the compound (II), R is the same as defined in the compound (I) and X is a leaving group. X is not particularly limited as long as X can act as a leaving group. Examples of X include halogen atoms such as fluorine atom, chlorine atom, bromine atom, and iodine atom; alkylsulfonyloxy group such as methanesulfonyloxy group; fluoroalkylsulfonyloxy groups such as trifluoromethanesulfonyloxy group and nonafluorobutanesulfonyloxy group; and arylsulfonyloxy groups such as toluenesulfonyloxy group.

When R in the compound (I) is a $C_{1-6}$ alkyl group substituted with one or more hydroxyl groups, a compound wherein R is a $C_{1-6}$ alkyl group substituted with a group that can be converted to hydroxyl group, may be used as the compound (II) to perform the reaction. Examples of the groups that can be converted to hydroxyl groups include a derivative whose hydroxyl group(s) is/are protected or an ester. In this case, after the reaction described above is completed, deprotection or reduction can be suitably performed by using any method well-known to those of skill in the art to convert the group to hydroxyl group(s).

The reaction described above may be also performed in solvent or under a solvent-free condition.

A solvent used in the reaction described above is not particularly limited as long as the solvent does not affect the reaction. Examples of solvents include ether-type solvents such as diethyl ether, diisopropyl ether, and tetrahydrofuran (THF); hydrocarbon-type solvents such as benzene, toluene, and xylene; halogen-containing hydrocarbon-type solvents such as dichloromethane and chloroform; and aprotic polar organic solvents such as N,N-dimethylformamide (DMF) and dimethyl sulfoxide (DMSO).

The reaction described above can be stopped by adding water to the reaction mixture. An aqueous solution of ammonium chloride may be used instead of the water to be added.

The compound (I) obtained from the reaction described above can be purified by using any method well-known to those of skill in the art. Examples of purification methods include column chromatography, gel filtration chromatography, and crystallization.

Another embodiment of the present invention is a pharmaceutical composition containing a compound (I).

The pharmaceutical composition can contain, in addition to the compound (I), any additives allowed to be added to a pharmaceutical preparation depending on a dosage form of interest. Examples of additives include an excipient, an isotonic agent, a stabilizer, a dissolution aid, a buffering agent, a pH modifier, a filler, a binder, a disintegrator, a lubricant, a coloring agent, and a flavoring agent.

When formulated into oral agents, including a tablet, a capsule, a granule, a powder, and a solution; and injections (which may be administered intravenously, intramuscularly, subcutaneously, or intraperitoneally), pharmaceutical compositions containing the compound or pharmaceutically acceptable salt thereof of the present embodiment are more easily formulated and also have higher reliability of pharmacological action than formulations containing roflumilast, because of good water solubility of the compound or pharmaceutically acceptable salt thereof. In addition, when formulated into transdermally absorbable preparations, including a patch, a poultice, a tape, an ointment, a gel, a lotion, a cream, and an aerosol, pharmaceutical compositions containing the compound or pharmaceutically acceptable salt thereof of the present embodiment are more easily formulated and also have higher reliability of pharmacological action than formulations containing roflumilast, because of good skin permeability of the compound or pharmaceutically acceptable salt thereof. Moreover, pharmaceutical compositions containing the compound or pharmaceutically acceptable salt thereof of the present embodiment may be formulated into an inhalation, a nasal preparation, an ophthalmic solution, and a suppository.

EXAMPLE

The present invention will be now described in more detail by way of Examples, Preparatory Examples, and Test Examples. It is noted that abbreviations used in Examples are conventional abbreviations well-known to those of skill in the art.

DMF: N,N-dimethylformamide
DMI: N,N-dimethylimidazolidinone
DMSO: dimethyl sulfoxide
n: normal
ODS: octadecyl silica gel
TBS: tert-butyldimethylsilyl
tert: tertiary
THF: tetrahydrofuran Chemical shifts of proton nuclear magnetic resonance spectrum ($^1$H-NMR) are described in δ unit (ppm) relative to tetramethylsilane (internal standard) and coupling constants are described in Hertz (Hz). Splitting patterns are described as s: singlet, d: doublet, t: triplet, q: quartet, m: multiplet, and br: broad.

Example 1

N-cyanomethyl-N-(3,5-dichloropyrid-4-yl)-3-cyclopropylmethoxy-4-difluoromethoxybenzamide

[Chemical Formula 4]

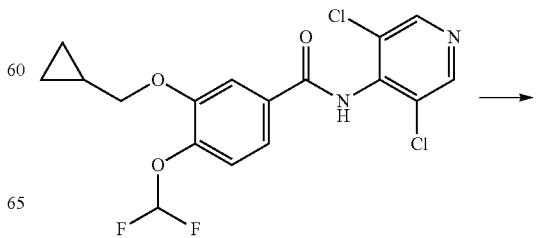

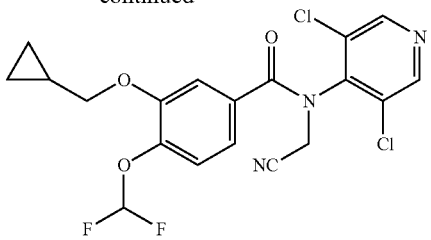

To a solution of 0.5 g (1.24 mmol) of roflumilast in dry DMF (5 mL) was added 56.4 mg of sodium hydride (60% dispersion in oil, 1.41 mmol) under nitrogen stream and the resulting mixture was stirred at room temperature for about 15 minutes. To the reaction mixture were added 0.172 mL (2.73 mmol) of chloroacetonitrile and 0.4 g (0.269 mmol) of sodium iodide and the resulting mixture was kept at room temperature for 2 hours. After completion of the reaction, 5 mL of water was added to the mixture and the resultant was extracted with mL of chloroform three times. The organic layer was washed with saturated saline and then dried over anhydrous sodium sulfate. The solvent was evaporated under reduced pressure. The residue was purified by silica gel column chromatography (ethyl acetate/n-hexane) and the resulting crude product was further purified by gel filtration chromatography to give 213 mg (0.481 mmol, yield 48%) of the title compound as a light yellow oil.

Melting point: 196° C.

$^1$H-NMR (500 MHz, CDCl$_3$) δ 0.35 (m, 2H), 0.65 (m, 2H), 1.21 (m, 1H), 3.78 (d, 2H), 4.65 (s, 2H), 6.61 (t, 1H), 6.87 (dd, 1H), 6.96 (d, 1H), 7.15 (d, 1H), 8.57 (s, 2H).

Preparatory Example 1

N-(3,5-dichloropyrid-4-yl)-N-methoxycarbonylm-ethyl-3-cyclopropylmethoxy-4-difluoromethoxyben-zamide

[Chemical Formula 5]

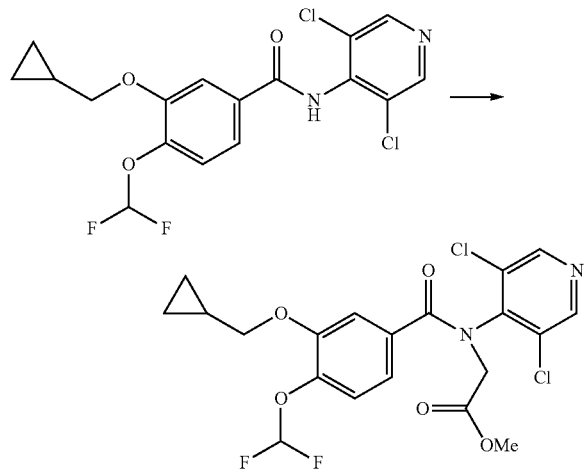

To a solution of 0.5 g (1.24 mmol) of roflumilast in dry DMF (5 mL) was added 56.5 mg of sodium hydride (60% dispersion in oil, 1.41 mmol) under nitrogen stream and the resulting mixture was stirred at room temperature for about 15 minutes. Then, 0.25 mL (2.73 mmol) of methyl bromo-acetate was added thereto and the resulting mixture was stirred at room temperature for 2.5 hours followed by stirring at 60° C. for 4.5 hours. The reaction mixture was left to cool to room temperature and 3 mL of water was added thereto. The mixture was extracted with 9 mL of chloroform three times. The organic layer was dried over anhydrous sodium sulfate. The solvent was evaporated under reduced pressure to give 649 mg (1.37 mmol) of the title compound as an orange oil.

Example 2

N-(3,5-dichloropyrid-4-yl)-N-(2-hydroxyethyl)-3-cyclopropylmethoxy-4-difluoromethoxybenzamide

[Chemical Formula 6]

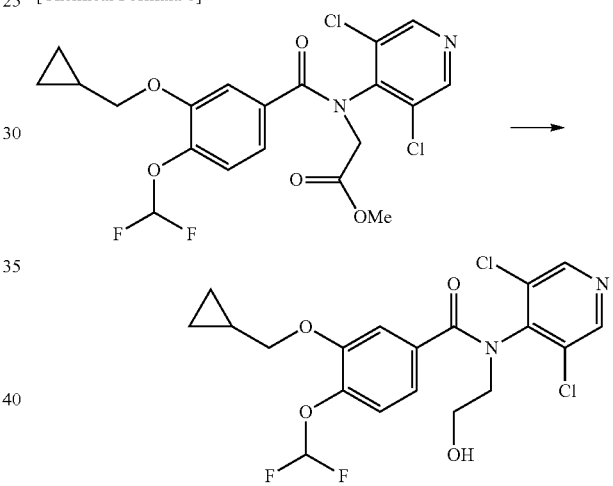

0.257 g (0.541 mmol) of the compound obtained in the Preparatory Example 1 and 0.111 g (7.93 mmol) of sodium borohydride was dissolved in 5 mL of methanol and 1.5 mL of TIE under nitrogen stream and the resulting mixture was stirred at room temperature for 24 hours. After completion of the reaction, the solvent was evaporated under reduced pressure. To the residue was added 5 mL of water and the mixture was extracted with 5 mL of chloroform three times. The organic layer was dried over anhydrous sodium sulfate and the solvent was then evaporated under reduced pressure. The residue was purified by silica gel column chromatography (chloroform) and the resulting crude product was further purified by gel filtration chromatography to give 50.3 mg (0.481 mmol, yield 2:1%) of the title compound as an oil.

Melting point: 97° C.

$^1$H-NMR (400 MHz, CDCl$_3$) δ 0.32 (m, 2H), 0.64 (m, 2H), 1.20 (m, 1H), 2.91 (brs, 1H), 3.76 (d, 2H), 3.95 (dd, 2H), 4.01 (d, 2H), 6.59 (t, 1H), 6.89 (dd, 1H), 6.93 (dd, 1H), 7.08 (d, 1H), 8.49 (s, 2H).

Example 3

N-(3,5-dichloropyrid-4-yl)-N-methyl-3-cyclopropyl-methoxy-4-difluoromethoxybenzamide

[Chemical Formula 7]

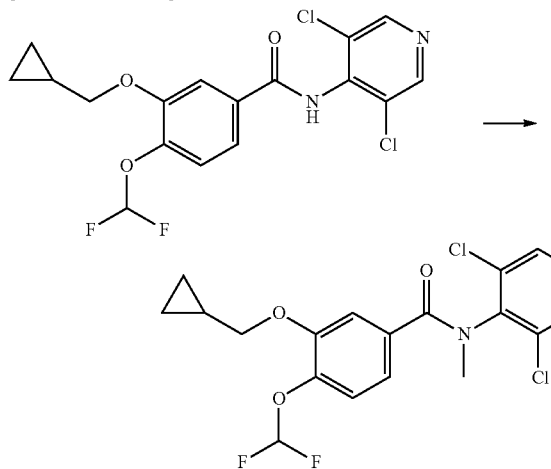

To a solution of 0.25 g (0.60 mmol) of roflumilast in dry DMF (5 mL) were added 72 mg of sodium hydride (60% dispersion in oil, 3.0 mmol) and 0.19 mL (3.0 mmol) of methyl iodide at 0° C. under nitrogen stream and the resulting mixture was stirred at room temperature for 12 hours. To the reaction mixture was added 3 mL of water and the resulting mixture was extracted with ethyl acetate three times. The organic layer was dried over anhydrous sodium sulfate and the solvent was evaporated under reduced pressure. The residue was purified using ODS column (acetonitrile/water/THF) and further desalted (NH cartridge, dichloromethane/methanol). The solvent was evaporated to give 0.16 g (0.38 mmol) of the title compound as a dark brown oil.

Melting point: 68° C.

$^1$H-NMR (400 MHz, CDCl$_3$) δ 0.32 (m, 2H), 0.63 (m, 2H), 1.20 (m, 1H), 3.31 (s, 3H), 3.76 (d, 2H), 6.57 (t, 1H), 6.90 (dd, 1H), 6.94 (d, 1H), 7.08 (d, 1H), 8.48 (s, 2H).

Preparatory Example 2-1

2,2-dimethyl-4-iodomethyl-1,3-dioxolane

[Chemical Formula 8]

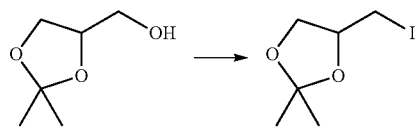

A mixture of 0.935 (7.57 mmol) of 2,2-dimethyl-1,3-dioxolane-4-methanol, 2.39 g (9.11 mmol) of triphenylphosphine, 1.54 g (22.7 mmol) of imidazole, and 2.30 g (18.1 mmol) of iodine was dissolved in 20 mL of dry toluene and stirred at 90° C. for 2 hours. The reaction solution was cooled to room temperature and the reaction was stopped by adding a saturated aqueous solution of sodium thiosulfate. The resulting reaction mixture was extracted with dichloromethane. The organic layer was washed with saturated saline and dried over anhydrous sodium sulfate. The solvent was then evaporated under reduced pressure to give 5.54 g of a white solid. The resulting solid was dispersed and washed in diethyl ether and hexane sequentially and then purified by silica gel column chromatography to give 1.04 g (4.28 mmol) of the title compound as a colorless oil.

Preparatory Example 2-2

N-(3,5-dichloropyrid-4-yl)-N-(2,2-dimethyl-1,3-dioxolan-4-yl)-3-cyclopropylmethoxy-4-difluoromethoxybenzamide

[Chemical Formula 9]

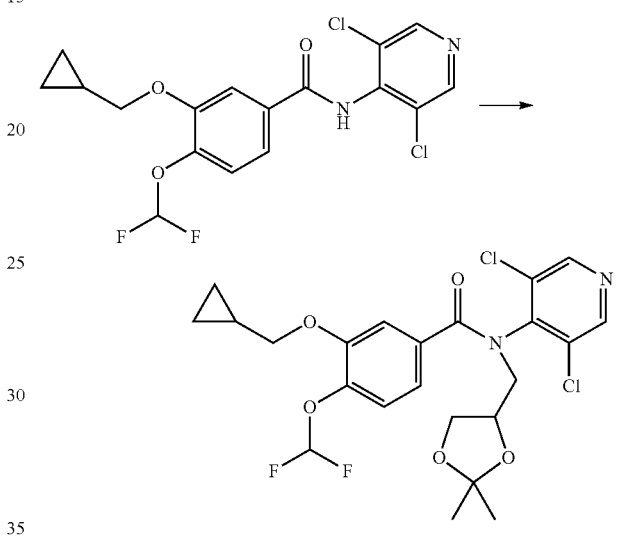

A solution of 0.32 g (0.8 mmol) of roflumilast, 0.29 g (1.21 mmol) of the compound obtained in the Preparatory Example 2-1, and 92 mg (1.64 mmol) of potassium hydroxide in dry DMSO (5 mL) was stirred at 100° C. for a day under nitrogen stream. After the reaction mixture was left to cool, chloroform was added to the reaction mixture and the resultant was further stirred. The deposited solid was filtered off. The filtrate was evaporated under reduced pressure and the residue was purified by silica gel column chromatography (ethyl acetate/n-hexane) to give 56.5 mg (0.11 mmol, yield 14%) of the title compound as an oil.

Example 4

N-(3,5-dichloropyrid-4-yl)-N-(2,3-dihydroxypropan-1-yl)-3-cyclopropylmethoxy-4-difluoromethoxybenzamide

[Chemical Formula 10]

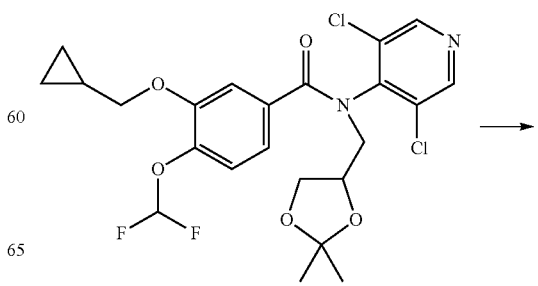

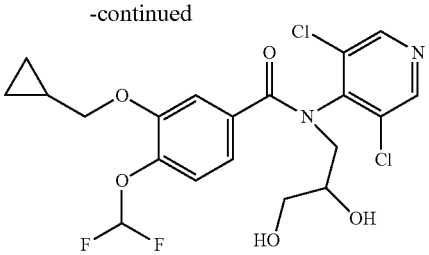

To a solution of 47 mg (0.092 mmol) of the compound obtained in the Preparatory Example 2-2 in THF (1.0 mL) was added 2 mL of 1M hydrochloric acid and the resulting mixture was stirred at room temperature for 12 hours. A saturated aqueous solution of sodium bicarbonate was added to the reaction mixture to adjust pH to 7 to 8. The reaction mixture was then extracted with chloroform three times. The organic layer was washed with saturated saline and then dried over anhydrous sodium sulfate. The solvent was evaporated under reduced pressure. The resulting residue was purified by silica gel column chromatography to give 28.2 mg (0.059 mmol, yield 64%) of the title compound.

$^1$H-NMR (500 MHz, CDCl$_3$) δ 0.33 (m, 2H), 0.64 (m, 2H), 1.20 (m, 1H), 1.26 (n, 2H), 2.55 (brs, 1H), 3.47 (brs, 1H), 3.75 (d, 2H), 3.95 (m, 3H), 6.59 (t, 1H), 6.89 (dd, 1H), 6.95 (d, 1H), 7.06 (d, 1H), 8.50 (s, 2H).

Preparatory Example 3-1

N-(3,5-dichloropyrid-4-yl)-N-(3-tert-butyldimethyl-silyloxypropan-1-yl)-3-cyclopropylmethoxy-4-difluoromethoxybenzamide

[Chemical Formula 11]

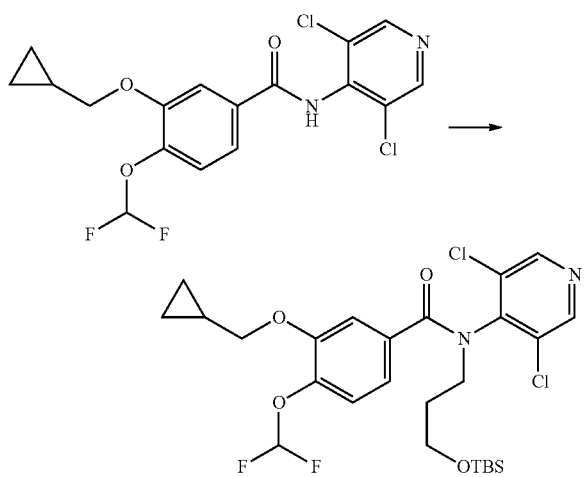

To a solution of 0.5 g (1.2 mmol) of roflumilast in DMI (5 mL) were added 139 mg (60% dispersion in oil, 3.5 mmol) of sodium hydride and 0.25 mL (2.9 mmol) of 3-tert-butyldimethylsilyloxypropyl bromide at room temperature under nitrogen stream. The mixture was heated to 70° C. and stirred for 12 hours. To the reaction mixture was added 3 mL of water. The reaction mixture was extracted with ethyl acetate three times. The resulting organic layer was washed with a saturated aqueous solution of sodium chloride and then dried over anhydrous sodium sulfate. The solvent was evaporated under reduced pressure. The residue was purified by silica gel column chromatography (heptane/ethyl acetate) to give 212 mg (0.368 mmol, yield 31%) of the title compound as a white solid.

Example 5

N-(3,5-dichloropyrid-4-yl)-N-(3-hydroxypropan-1-yl)-3-cyclopropylmethoxy-4-difluoromethoxybenzamide

[Chemical Formula 12]

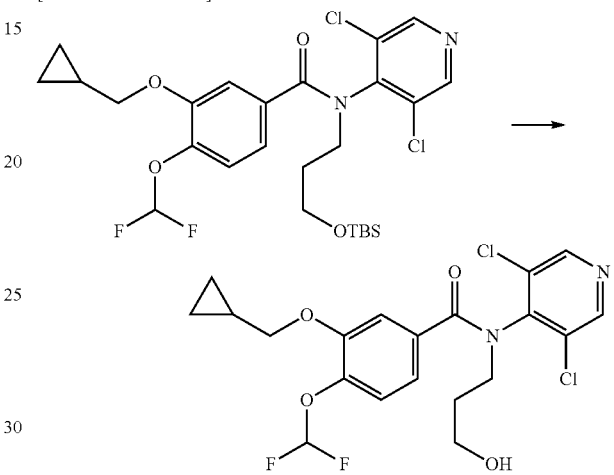

In 3 mL of a mixed solution of methanol and concentrated hydrochloric acid (volume ratio 97:3) was dissolved 180 mg (0.31 mmol) of the compound obtained in the Preparatory Example 34 and the resulting mixture was stirred at room temperature for an hour. The reaction mixture was concentrated under reduced pressure and purified by silica gel column chromatography (heptane/ethyl acetate). The resulting residue was dissolved in ethyl acetate and washed with a saturated aqueous solution of sodium bicarbonate to give 86 mg (0.186 mmol, yield 60%) of the title compound as a white solid.

$^1$H-NMR (400 MHz, CDCl$_3$) δ 0.32 (m, 2H), 0.63 (m, 2H), 1.20 (m, 1H), 1.84 (m, 2H), 3.75 (d, 2H), 3.78 (t, 2H), 3.98 (t, 2H), 6.58 (t, 1H), 6.88 (dd, 1H), 6.94 (d, 1H), 7.05 (d, 1H), 8.49 (s, 2H).

Example 6

N-(3,5-dichloropyrid-4-yl)-N-methoxymethyl-3-cyclopropylmethoxy-4-difluoromethoxybenzamide

[Chemical Formula 13]

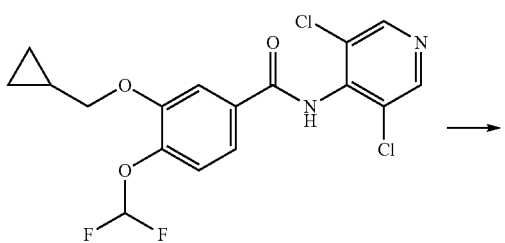

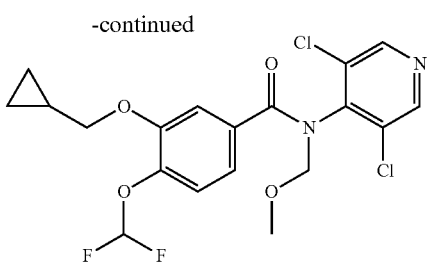

To a solution of 505 mg (1.25 mmol) of roflumilast in dry DMF (5 mL) was added under nitrogen stream 69 mg (60% dispersion in oil, 1.73 mmol) of sodium hydride followed by addition of 0.3 mL (3.67 mmol) of bromomethyl methyl ether. The mixture was stirred at room temperature for 2 hours. To the reaction mixture was added 5 mL of water and the resulting mixture was extracted with chloroform three times to give organic layer. The organic layer was dried over anhydrous sodium sulfate. The solvent was then evaporated under reduced pressure to give a crude oil product. The crude product was purified by silica gel column chromatography (n-hexane/dichloromethane). The resulting light yellow solid was recrystallized from dichloromethane/n-hexane to give 188 mg (0.42 mmol, yield 34%) of the title compound as a white solid.

$^1$H-NMR (500 MHz, CDCl$_3$) δ 0.32 (m, 2H), 0.64 (m, 2H), 1.20 (m, 1H), 3.60 (s, 3H), 3.75 (d, 2H), 5.26 (s, 2H), 6.57 (t, 1H), 6.92 (dd, 1H), 6.95 (d, 1H), 7.10 (d, 1H), 8.50 (s, 2H).

Reference Example 1

N-carbamoylmethyl-N-(3,5-dichloropyrid-4-yl)-3-cyclopropylmethoxy-4-difluoromethoxybenzamide

[Chemical Formula 14]

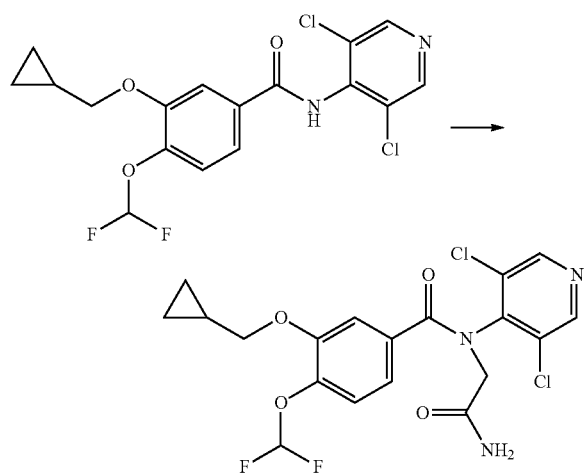

A solution of 0.5 g (1.24 mmol) of roflumilast in dry DMF (5 mL) was added 55.3 mg (60% dispersion in oil, 1.38 mmol) of sodium hydride under nitrogen stream and the resulting mixture was stirred at room temperature for about 15 minutes. To the reaction mixture were added 0.25 (1.63 mmol) of chloroacetamide and 0.41 g (2.74 mmol) of sodium iodide and the resulting mixture was stirred at room temperature for 12 hours. To the reaction mixture was added 5 mL of water and the mixture was extracted with 5 mL of chloroform three times. The organic layer was washed with saturated saline and then dried over anhydrous sodium sulfate. The solvent was evaporated under reduced pressure. The residue was purified by silica gel column chromatography (methanol/dichloromethane) and further purified by gel filtration chromatography to give 94 mg (0.204 mmol, yield 16%) of the title compound as a light yellow solid.

Melting point: 90.99° C.

$^1$H-NMR (500 MHz, DMSO-d$_6$) δ 0.38 (m, 2H), 0.56 (m, 2H), 1.23 (m, 1H), 3.91 (d, 2H), 4.35 (s, 2H), 7.15 (t, 1H), 7.19 (d, 1H), 7.48 (s, 1H), 7.49 (dd, 1H), 7.59 (d, 1H), 7.78 (s, 1H), 8.28 (s, 2H).

Reference Example 2

N-carboxymethyl-N-(3,5-dichloropyrid-4-yl)-3-cyclopropylmethoxy-4-difluoromethoxybenzamide

[Chemical Formula 15]

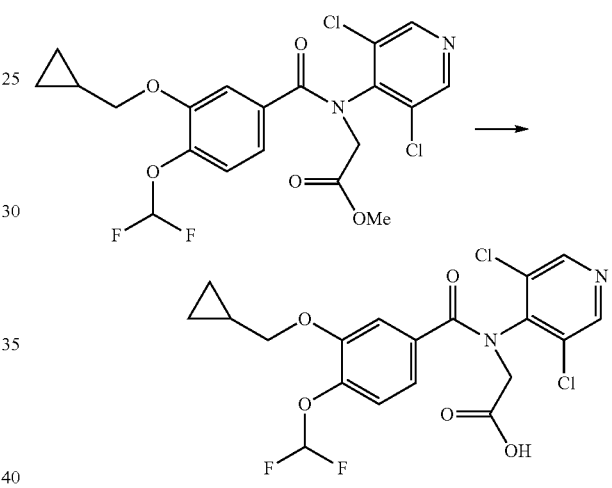

In 14 mL of methanol was dissolved 0.65 g (1.37 mmol) of the compound obtained in the Preparatory Example 1. To the mixture was added 14 of 1N sodium hydroxide aqueous solution at room temperature and the mixture was stirred for 5 minutes. The reaction mixture was concentrated under reduced pressure and 1N hydrochloric acid was added thereto until pH of the aqueous layer reached pH 1. The mixture was extracted with 10 mL of chloroform three times. The resulting organic layers were combined and dried over anhydrous sodium sulfate. The solvent was evaporated under reduced pressure to give a light yellow residue. To the resulting residue was added 5 mL of 1N sodium hydroxide and the mixture was washed with 5 mL of chloroform twice. A solution of 1N hydrochloric acid was added thereto until pH of the aqueous layer reached pH 1. The mixture was extracted with 5 mL of chloroform three times. The resulting organic layer was dried over anhydrous sodium sulfate and the solvent was evaporated under reduced pressure. The resulting residue was purified by silica gel column chromatography (chloroform/methanol) to give 0.342 mg (0.740 mmol, yield 54%) of the title compound as a light yellow amorphous substance.

Melting point: 182° C.

$^1$H-NMR (500 MHz, CDCl$_3$) δ 0.32 (m, 2H), 0.64 (m, 2H), 1.20 (m, 1H), 3.76 (d, 2H), 4.45 (s, 2H), 6.61 (t, 1H), 6.92 (dd, 1H), 6.96 (d, 1H), 7.15 (d, 1H), 8.50 (s, 2H).

Test Example 1: In Vitro Metabolism Test

A human liver enzyme fraction was added to 100 mmol/L Tris-HCl buffer containing coenzymes (NADPH-producing) so as to achieve the concentration of 0.5 mg protein/mL and the resultant was pre-incubated at 37° C. for 5 minutes. A test compound was added to this solution so as to achieve the concentration of 0.1 μmol/L and the resultant was incubated at 37° C. for an hour. The reaction was then stopped by adding water-cooled acetonitrile. The resulting solution was filtered and then quantified by using LC-MS/MS to calculate the metabolic rate (%) into roflumilast. It is noted that "with heat treatment" in Table 1 means using a human liver enzyme fraction subjected to heat treatment before adding to thereby inactivate a metabolic enzyme therein.

The results are shown in Table 1. Numerical values in Table 1 represent metabolic rates (%) into rofiumilast. The compounds of Examples 1 to 6 were metabolized to roflumilast by enzymes from human liver. Roflumilast was not produced when metabolic enzymes were inactivated by heat treatments prior to using the human liver enzyme fractions. On the other hand, the compounds of Reference Examples 1 and 2 did not produce roflumilast when treated with the human liver enzyme fractions.

TABLE 1

| | Human Liver Enzyme Fraction | |
| --- | --- | --- |
| | with heat treatment | without heat treatment |
| Reference Example 1 | 0 | 0 |
| Reference Example 2 | 0 | 0 |
| Example 1 | 0 | 66.8 |
| Example 2 | 0 | 12.2 |
| Example 3 | 0 | 77.8 |
| Example 4 | 0 | 2.0 |
| Example 5 | 0 | 3.3 |
| Example 6 | 0 | 60.3 |

Test Example 2: Evaluation Test of Water Solubility

An excessive amount of a test compound was added to 10 mL of phosphate buffer (pH 7) and the resultant was ultrasonicated for 30 minutes. The resulting suspension was filtered and 0.5 mL of acetonitrile was added to 0.5 mL of the filtrate to obtain a test solution. The concentration of the test compound in the test solution was determined by high performance liquid chromatography to calculate the saturated solubility. Roflumilast was used in Comparative Example 1.

The results are shown in Table 2. It has been revealed that the water solubilities of the compounds of Examples 1 to 3 and Reference Examples 1 and 2 are four times or more as high as the water solubility of roflumilast.

TABLE 2

| | Saturated Solubility [μg/mL] | Ratio to Roflumilast |
| --- | --- | --- |
| Reference Example 1 | 16.58 | 44.5 |
| Reference Example 2 | 611.8 | 1640.2 |
| Example 1 | 1.643 | 4.4 |
| Example 2 | 12.46 | 33.4 |
| Example 3 | 9.7 | 26.0 |
| Comparative Example 1 | 0.373 | 1 |

Test Example 3: Evaluation Test of Skin Permeability

Skin was excised from the back of a hairless mouse and the section of the skin was placed in a Franz diffusion cell (glass cell) so that a solution of each of test compounds (compounds of Examples, Comparative Example, or Reference Examples) was contacted with the epidermal side of the section of the skin (applied area: 1 cm²). Phosphate buffered physiological saline (PBS) was used as a flow solution. The flow rate was set to 5 mL/hour and the temperature of thermoregulated bath was set to 32° C. Next, dimethyl sulfoxide was added to achieve the concentration of the test compound of 1 w/w % and the resultant was stirred thoroughly to prepare a solution of the test compound. The donor chamber of the Franz diffusion cell was charged with 100 μL of the resulting solution of the test compound. The flow solution was sampled every 2 hours until 24 hours after the charge of the test compound solution. The flow solutions sampled every 2 hours were diluted two-fold by adding acetonitrile and the diluted solution was centrifuged to give supernatants as an HPLC analytical sample. Each of the resulting analytical samples was analyzed by high performance liquid chromatography to calculate the maximum skin permeation rate (Jmax) and the cumulative amount of permeation for 24 hours. Roflumilast was used in Comparative Example 1.

The results are shown in Table 3. The compound of Comparative Example 1 (roflumilast) showed no skin permeability even after 24 hours while the compounds of Examples and Reference Examples showed sufficient skin permeability. The time-dependent change of cumulative amounts of permeation (μg/cm²) of the test compounds is shown in FIG. 1. The compounds of Examples 1 to 3, 5, and 6 showed high skin permeability as compared with the compound of Comparative Example 1 (roflumilast).

TABLE 3

| | Jmax [μg/cm²/hr] | Cumulative Amount of Permeation for 24 hours [μg/cm²] |
| --- | --- | --- |
| Reference Example 1 | 0.9 | 7.2 |
| Reference Example 2 | 9.5 | 56.9 |
| Example 1 | 1.2 | 12.1 |
| Example 2 | 10.7 | 157.7 |
| Example 3 | 3.2 | 51.0 |
| Example 5 | 8.5 | 163.5 |
| Example 6 | 1.2 | 17.6 |
| Comparative Example 1 | 0.0 | 0.0 |

The invention claimed is:

1. A compound represented by the formula (I) or a pharmaceutically acceptable salt thereof:

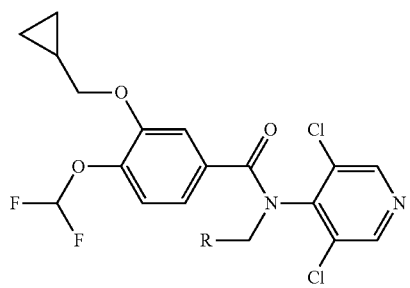

(I)

wherein R is a $C_{1-6}$ alkyl group optionally substituted with one or more hydroxyl groups, a $C_{1-6}$ alkoxy group, or a cyano group.

2. The compound or pharmaceutically acceptable salt thereof according to claim 1, wherein R is a $C_{1-6}$ alkyl group optionally substituted with one or more hydroxyl groups, or a cyano group.

3. The compound or pharmaceutically acceptable salt thereof according to claim 1, wherein R is a hydroxymethyl group, a methoxy group, or a cyano group.

4. The compound or pharmaceutically acceptable salt thereof according to claim 1, wherein R a hydroxymethyl group, or a cyano group.

5. A pharmaceutical composition comprising the compound represented by the formula (II) or pharmaceutically acceptable salt thereof:

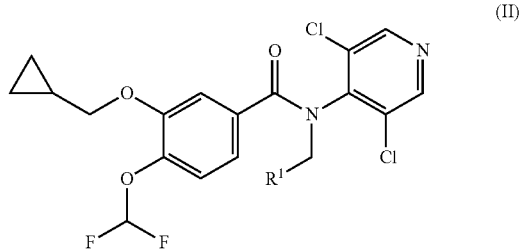

(II)

wherein $R^1$ is a hydrogen atom, a $C_{1-6}$ alkyl group optionally substituted with one or more hydroxyl groups, a $C_{1-6}$ alkoxy group, or a cyano group.

6. The pharmaceutical composition according to claim 5, wherein the pharmaceutical composition is a PDE4 inhibitor.

7. The pharmaceutical composition according to claim 5, wherein the pharmaceutical composition is a therapeutic agent for a disease or condition against which inhibiting PDE4 is effective.

8. The pharmaceutical composition according to claim 7, wherein the disease or condition is a chronic obstructive pulmonary disease.

9. A method of treating a disease or condition against which inhibiting PDE4 is effective, comprising administering the pharmaceutical composition according to claim 5 to a subject in need thereof.

10. The method according to claim 9, wherein the disease or condition is a chronic obstructive pulmonary disease.

* * * * *